United States Patent
Shiomi et al.

(10) Patent No.: US 6,825,374 B2
(45) Date of Patent: Nov. 30, 2004

(54) ALKYL-SUBSTITUTED TETRACYCLODODECENECARBOXYLIC ACID ESTERS, (METH)ACRYLIC ACID ADDITION PRODUCTS THEREOF, AND METHODS FOR PRODUCING THE SAME

(75) Inventors: Taiichi Shiomi, Wakayama (JP);
Takafumi Tsujigami, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 136 days.

(21) Appl. No.: 10/251,725

(22) Filed: Sep. 20, 2002

(65) Prior Publication Data

US 2003/0073864 A1 Apr. 17, 2003

(30) Foreign Application Priority Data

Oct. 15, 2001 (JP) ........................................ 2001-317292

(51) Int. Cl.⁷ .............................................. C07C 69/74
(52) U.S. Cl. ...................................................... 560/116
(58) Field of Search ........................................ 560/116

(56) References Cited

U.S. PATENT DOCUMENTS 6,287,746 B1    9/2001   Nakano et al.

FOREIGN PATENT DOCUMENTS

| JP | 48-49753 | 7/1973 |
| JP | 04-198154 | 7/1992 |
| JP | 10-307400 | 11/1998 |
| JP | 2001-011122 | 1/2001 |

*Primary Examiner*—Paul J. Killos
(74) *Attorney, Agent, or Firm*—Knobbe, Martens Olson & Bear LLP

(57) ABSTRACT

The present invention provides alkyl-substituted tetracyclododecenecarboxylic acid esters presented by the general formula (I):

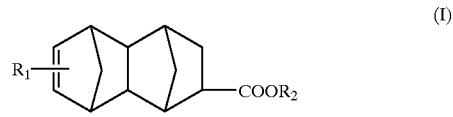

(I)

wherein $R_1$ is an alkyl group having 1 to 4 carbon atoms and $R_2$ is a hydrocarbon group having 1 to 12 carbon atoms. Further, the represent invention provides (meth)acrylic acid addition products of alkyl-substituted tetracyclododecenecarboxylic acid esters represented by the general formula (II):

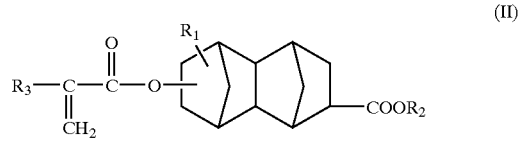

(II)

wherein $R_1$ is an alkyl group having 1 to 4 carbon atoms, $R_2$ is a hydrocarbon group having 1 to 12 carbon atoms, and $R_3$ is a hydrogen atom or a methyl group.

7 Claims, 2 Drawing Sheets

ALKYL-SUBSTITUTED TETRACYCLODODECENECARBOXYLIC ACID ESTERS, (METH)ACRYLIC ACID ADDITION PRODUCTS THEREOF, AND METHODS FOR PRODUCING THE SAME

BACKGROUND OF THE INVENTION

1. Field of the Invention

The present invention relates to novel tetracyclododecenecarboxylic acid esters and (math) acrylic acid addition products thereof and methods for producing the same.

Such tetracyclododecenecarboxylic acid esters according to the present invention have one alkyl group and one carboxylic acid ester group on a bulky bridged cyclic hydrocarbon skeleton which has excellent moisture-resistance, heat-resistance, optical characteristics, and other properties. Similarly (meth)acryl acid addition products of the tetracyclododecenecarboxylic acid esters have one carboxylic acid ester group and one (meth) acryl group on a bulky bridged cyclic hydrocarbon skeleton which has excellent moisture-resistance, heat-resistance, optical characteristics, and other properties. Thus, they are useful, for example, as a material for photosensitive resists for semiconductor fine processing or the like and a material for optical material resins.

2. Description of the Related Art

Recently, characteristic requirements for photosensitive resists and optical material resins have been increasingly diversified and heightened. For example, improvements are strongly required in capacity of photosensitive resists in fine processing corresponding to short wave lasers as well as in optical characteristics, heat resistance and mechanical strength of resins for optical materials.

It is known that when tetracyclododecenecarboxylic acid derivatives are used as a polymer component of the above-mentioned photosensitive resists or optical material resins, capability in fine processing and characteristics such as transparency, moisture-resistance and heat-resistance can be improved. Accordingly, today, requirements in capabilities of tetracyclododecenecarboxylic acid derivatives for photosensitive resists and optical material resins have been also increasingly diversified and heightened.

As for tetracyclododecenecarboxylic acid derivatives, for example, Japanese Patent Application Laid-open No. 1973-49753 describes that 8-carboxymethyltetracyclo[4.4.0.1$^{2,5}$.1$^{7,10}$]-dodeca-3-ene is obtained from cyclopentadiene or methyl acrylate. Japanese Patent Application Laid-open No. 1992-198154 described that 8-methyl-8-carboxymethyltetracyclo[4.4.0.1$^{2,5}$.1$^{7,10}$]-dodeca-3-ene or 8-methyl-8-carboxyethyltetracyclo[4.4.0.1$^{2,5}$1$^{7,10}$]-dodeca-3-ene are obtained by the Diels-Alder reaction with dicyclopentadiene and methyl methacrylate or ethyl methacrylate.

Further, Japanese Patent Application Laid-open No. 1998-307400 describes that t-butoxycarbonyltetracyclo[4.4.0.1$^{2,5}$.1$^{7,10}$]-3-dodecanyl methacrylate is obtained from hydroxy-8-t-butoxycarbonyltetracyclo[4.4.0.1$^{2,5}$.1$^{7,10}$]-dodecane and methacryloyl chloride. Further, Japanese Patent Application Laid-open No. 2001-11122 describes methoxycarbonyltetracyclo[4.4.0.1$^{2,5}$.1$^{7,10}$]-dodecyl methacrylate.

However, so far, there has been no report on a compound having an alkyl group on an unsaturated ring of 8-alkoxycarbonyltetracyclo[4.4.0.1$^{2,5}$.1$^{7,10}$]dodeca-3-ene skeleton or a (meth)acrylic acid addition product of this compound, namely 8-alkoxycarbonyltetracyclo[4.4.0.1$^{2,5}$.1$^{7,10}$]-3-dodecanes having a (meth)acryloyl group.

SUMMARY OF THE INVENTION

The present invention was accomplished under the above-mentioned circumstances regarding tetracyclododecenecarboxylic acid derivatives. An objective of the present invention is to provide novel tetracyclododecenecarboxylic acid derivatives, in particular, novel tetracyclododecenecarboxylic acid esters and (math)acrylic acid addition products thereof, which are useful as a raw material for photosensitive resists for semiconductor fine processing or the like and as a raw material for optical material resins.

The present invention provides alkyl-substituted tetracyclododecenecarboxylic acid esters represented by the general formula (I)

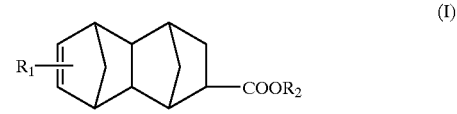

wherein $R_1$ is an alkyl group having 1 to 4 carbon atoms and $R_2$ is a hydrocarbon group having 1 to 12 carbon atoms.

Further, the present invention provides (meth)acrylic acid addition products of alkyl-substituted tetracyclododecenecarboxylic acid esters, represented by the general formula (II)

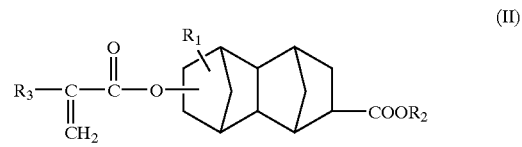

wherein $R_1$ is an alkyl group having 1 to 4 carbon atoms, $R_2$ is a hydrocarbon group having 1 to 12 carbon atoms, and $R_3$ is a hydrogen atom or a methyl group.

Further, the present invention provides methods of producing alkyl-substituted tetracyclododecenecarboxylic acid esters represented by the abovementioned general formula (I) characterized in that an alkylcyclopentadiene represented by the general formula (III)

wherein $R_1$ is an alkyl group having 1 to 4 carbon atoms and a norbornenecarboxylic acid ester represented by the general formula (IV)

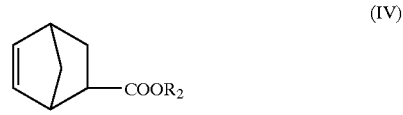

wherein $R_2$ is a hydrocarbon group having 1 to 12 carbon atoms are subjected to the Diels-Alder reaction.

Further, the present invention provides methods of producing (meth)acrylic acid addition products of alkyl-substituted tetracyclododecenecarboxylic acid esters represented by the abovementioned general formula (II) characterized in that an alkyl-substituted tetracyclododecenecarboxylic acid ester represented by the abovementioned general formula (I) and (meth)acrylic acid are reacted in the presence of an acid catalyst.

DETAILED DESCRIPTION OF THE PREFERRED EMBODIMENT

Figure 1:
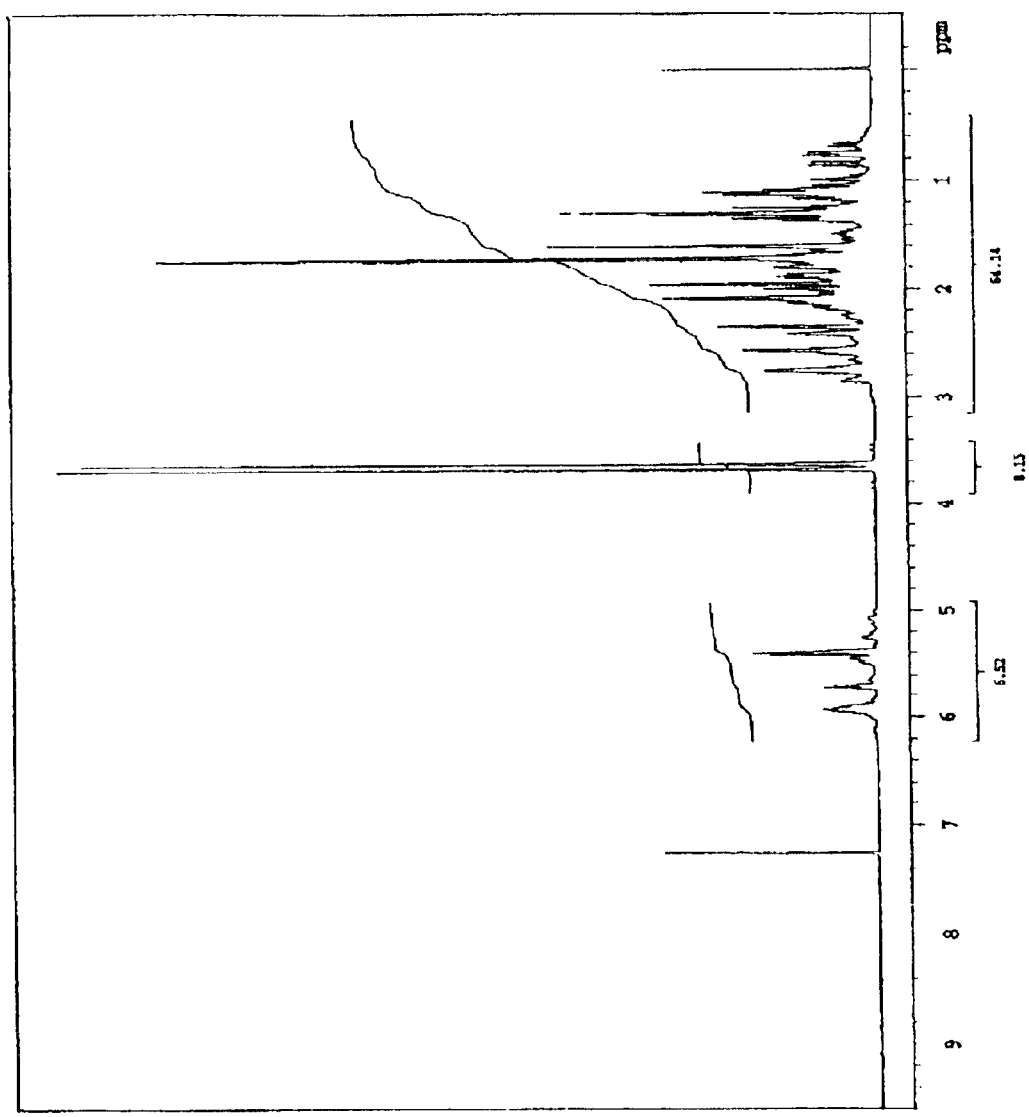
FIG. 1 shows the $^1$H-NMR spectrum of methyl-8-methoxycarbonyltetracyclo[4.4.0.1$^{2,5}$.1$^{7,10}$]dodeca-3-ene according to the present invention.

In the present invention, the term "(meth)acrylic acid" refers to acrylic acid or methacrylic acid, and the term "(meth)acryloyl group" refers to acryloyl group or methacryloyl group.

Alkyl-substituted tetracyclododecenecarboxylic acid esters according to the present invention are represented by the general formula (I)

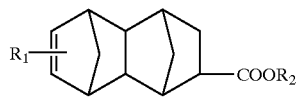

(I)

wherein $R_1$ is an alkyl group having 1 to 4 carbon atoms and $R_2$ is a hydrocarbon group having 1 to 12 carbon atoms.

In alkyl-substituted tetracyclododecenecarboxylic acid esters represented by the general formula (I) above, $R_1$ is an alkyl group having 1 to 4 carbon atoms, more specifically, a methyl group, ethyl group, propyl group or butyl group. The propyl group and butyl group can be either linear or branched. However, in the present invention, the abovementioned alkyl group $R_1$ is preferably a methyl group or ethyl group.

$R_2$ is a hydrocarbon group having 1 to 12 carbon atoms, more specifically, preferably an alkyl group having 1 to 4 carbon atoms, for example, a linear or branched alkyl group such as methyl group, ethyl group, propyl group and butyl group; a substituted or unsubstituted cycloalkyl group having 5 to 7 carbon atoms, such as cylopentyl group and cyclohexyl group; a substituted or unsubstituted aryl group having 6 to 14 carbon atoms, such as a phenyl group, naphthyl group, biphenyl group, and phenanthryl group; and a substituted or unsubstituted bridged cyclic hydrocarbon group having 7 to 14 carbon atoms, such as bicyclo[2.2.1]hept-2-ene-2-yl group and adamantyl group. However, in the present invention, the abovementioned hydrocarbon group $R_2$ is preferably an alkyl group having 1 to 4 carbon atoms.

Accordingly, preferable examples of alkyl-substituted tetracyclododecenecarboxylic acid esters of the present invention include (1) methyl-8-methoxycarbonyltetracyclo[4.4.0.1$^{2,5}$.1$^{7,10}$]dodeca-3-ene

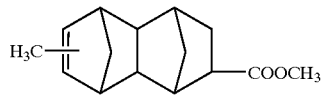

(1)

(2) ethyl-8-ethoxycarbonyltetracyclo[4.4.0.1$^{2,5}$.1$^{7,10}$]dodeca-3-ene

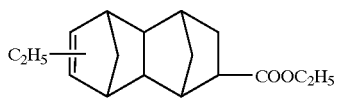

(2)

(3) methyl-8-t-butoxycarbonyltetracyclo[4.4.0.1$^{2,5}$.1$^{7,10}$]dodeca-3-ene

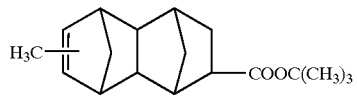

(3)

(4) propyl-8-neopentyloxycarbonyltetracyclo[4.4.0.1$^{2,5}$.1$^{7,10}$]dodeca-3-ene

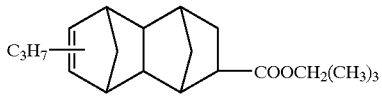

(4)

(5) methyl-8-cyclopentyloxycarbonyltetracyclo[4.4.0.1$^{2,5}$.1$^{7,10}$]dodeca-3-ene

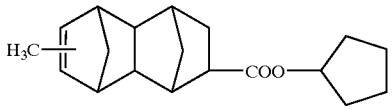

(5)

(6) methyl-8-cyclohexyloxycarbonyltetracyclo[4.4.0.1$^{2,5}$.1$^{7,10}$]dodeca-3-ene

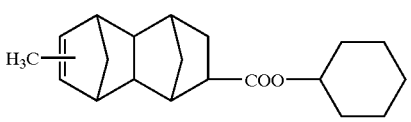

(6)

(7) methyl-8-phenyloxycarbonyltetracyclo[4.4.0.1$^{2,5}$.1$^{7,10}$]dodeca-3-ene

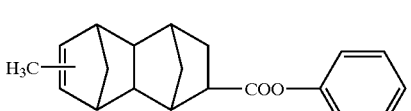

(7)

(8) methyl-8-(2-naphthyl)oxycarbonyltetracyclo[4.4.0.1$^{2,5}$.1$^{7,10}$]dodeca-3-ene (8)

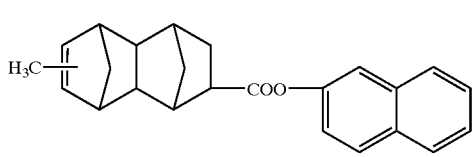

(9) methyl-8-(1-adamantyl)oxycarbonyltetracyclo[4.4.0.1$^{2,5}$.1$^{7,10}$]dodeca-3-ene, and (9)

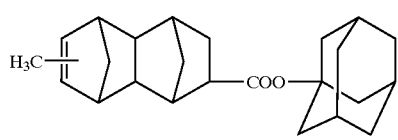

(10) methyl-8-(2-methyl-2-adamantyl)oxycarbonyltetracyclo[4.4.0.1$^{2,5}$.1$^{7,10}$]dodeca-3-ene (10)

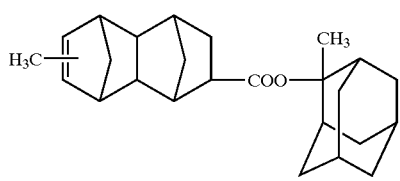

Further, (meth)acrylic acid addition products of the abovementioned alkyl-substituted tetracyclododecenecarboxylic acid esters according to the present invention, namely alkyl-8-alcoxycarbonyltetracyclododecanyl (meth)acrylates are represented by the general formula (II)

(II)

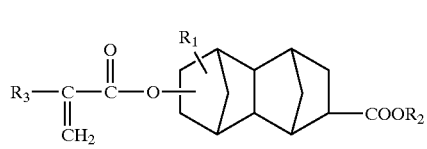

wherein R$_1$ is an alkyl group having 1 to 4 carbon atoms, R$_2$ is a hydrocarbon group having 1 to 12 carbon atoms, and R$_3$ is a hydrogen atom or a methyl group.

In (meth)acrylic acid addition products of alkyl-substituted tetracyclododecenecarboxylic acid esters represented by the general formula (II) above, the alkyl group R$_1$ and the hydrocarbon group R$_2$ are the same as described above. R$_3$ is a hydrogen atom or a methyl group.

Accordingly, preferable examples of (meth)acrylic acid addition products of alkyl-substituted tetracyclododecenecarboxylic acid esters according to the present invention include

(11) methyl-8-methoxycarbonyltetracyclo[4.4.0.1$^{2,5}$.1$^{7,10}$]dodecanyl acrylate (11)

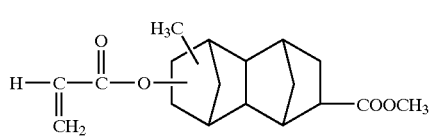

(12) ethyl-8-ethoxycarbonyltetracyclo[4.4.0.1$^{2,5}$.1$^{7,10}$]dodecanyl acrylate (12)

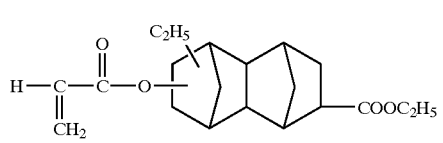

(13) methyl-8-t-butoxycarbonyltetracyclo[4.4.0.1$^{2,5}$.1$^{7,10}$]dodecanyl acrylate (13)

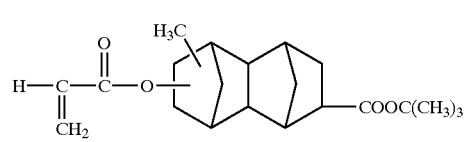

(14) propyl-8-neopentyloxycarbonyltetracyclo[4.4.0.1$^{2,5}$.1$^{7,10}$]dodecanyl acrylate (14)

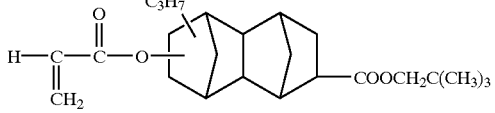

(15) methyl-8-cyclopentyloxycarbonyltetracyclo[4.4.0.1$^{2,5}$.1$^{7,10}$]dodecanyl acrylate (15)

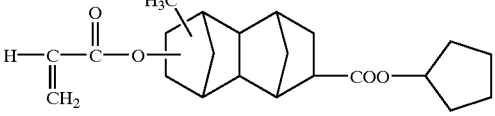

(16) methyl-8-cyclohexyloxycarbonyltetracyclo[4.4.0.1$^{2,5}$.1$^{7,10}$]dodecanyl acrylate (16)

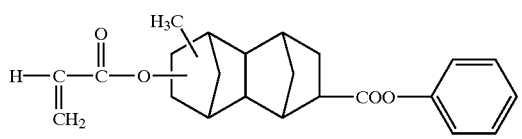

(17) methyl-8-phenyloxycarbonyltetracyclo[4.4.0.1$^{2,5}$.1$^{7,10}$]dodecanyl acrylate (17)

(18) methyl-8-(2-naphthyl)oxycarbonyltetracyclo[4.4.0.1$^{2,5}$.1$^{7,10}$]dodecanyl acrylate (18)

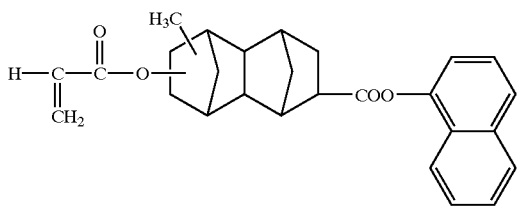

(19) methyl-8-(1-adamantyl)oxycarbonyltetracyclo[4.4.0.1$^{2,5}$.1$^{7,10}$]dodecanyl acrylate, and (19)

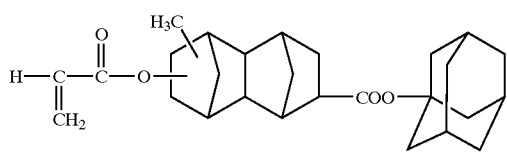

(20) methyl-8-(2-methyl-2-adamantyl)oxycarbonyltetracyclo[4.4.0.1$^{2,5}$.1$^{7,10}$]-3-dodecanyl acrylate.

(20)

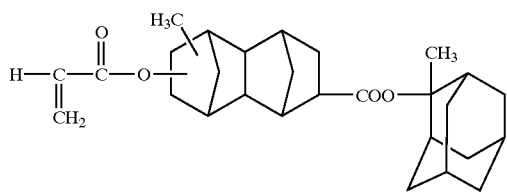

Alkyl-substituted alkoxycarbonyltetracyclododecenes represented by the abovementioned general formula (I) can be obtained according to the present invention by subjecting an alkylcyclopentadiene represented by the general formula (III)

(III)

wherein $R_1$ is the same as described above and a norbornenecarboxylic acid ester represented by the general formula (IV)

(IV)

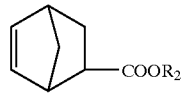

wherein $R_2$ is the same as described above to the Diels-Alder reaction.

In alkylcyclopentadienes represented by the general formula (III) above, $R_1$ is the same as described above. Accordingly, examples of such compounds include methylcyclopentadiene, ethylcyclopentadiene and propylcyclopentadiene. However, in particular, methylcyclopentadiene is preferably used. In place of these alkylpentadienes, alkyl-substituted dicyclopentadienes that produce their alkylcyclopentadienes by heat decomposition can also be used in the same way.

In norbornenecarboxylic acid esters represented by the general formula (IV) above, $R_2$ is the same as described above. Accordingly, examples of such compounds include 5-methoxycarbonylbicyclo[2.2.1]hept-2-ene 5-ethoxycarbonylbicyclo[2.2.1]hept-2-ene 5-propoxycarbonylbicyclo[2.2.1]hept-2-ene 5-t-butoxycarbonylbicyclo[2.2.1]hept-2-ene 5-cyclopentyloxycarbonylbicyclo[2.2.1]hept-2-ene 5-cyclohexyloxycarbonylbicyclo[2.2.1]hept-2-ene 5-phenyloxycarbonylbicyclo[2.2.1]hept-2-ene 5-naphthyloxycarbonylbicyclo[2.2.1]hept-2-ene 5-(1-adamantyl)oxycarbonylbicyclo[2.2.1]hept-2-ene, and 5-(2-methyl-2-adamantyl)oxycarbonylbicyclo[2.2.1]hept-2-ene.

In the Diels-Alder reaction of the abovementioned alkylcyclopentadiene and the abovementioned norbornenecarboxylic acid ester, the norbornenecarboxylic acid ester is generally used in the range of 0.15 to 5 molar parts, preferably 0.2 to 2 molar parts, and most preferably 0.3 to 0.7 molar part per one molar part of alkylcyclopentadiene.

The purity of the abovementioned material, norbornenecarboxylic acid ester, is preferably more than 95% to prevent drastic decrease in reaction utilization efficiency of alkylcyclopentadiene caused by bi-product production.

The reaction temperature is in the range of 80 to 250° C., preferably 130 to 220° C., and most preferably 180 to 200° C. Further, the reaction time is in the range of about 0.5 to 20 hours, preferably about 1 to 10 hours, and most preferably about 2 to 4 hours. The reaction pressure is in the range of 0.5 to 40 Mpa, preferably 3 to 30 Mpa.

The Diels-Alder reaction of the abovementioned alkylcyclopentadiene and the abovementioned norbornenecarboxylic acid ester can be carried out by either a batch system or a continuous system. In a batch system, for example, specified amounts of alkylcyclopentadiene and norbornenecarboxylic acid ester are placed together in an autoclave and reacted by heating under pressure.

In the reaction, a conventionally known thermal-polymerization preventing agent, such as hydroquinone and 4-methoxyphenol, can be added to the reaction system. In order to prevent coagulation of materials or reaction products, an aromatic solvent such as toluene can be used as a reaction solvent, if necessary.

The reaction product obtained by the Diels-Alder reaction is purified, if necessary. For example, after the reaction is completed, the resulting reaction mixture is distilled under reduced pressure at a temperature at which the reaction product can be isolated from unreacted materials and by-product polymers, for example at about 40 to 80° C., to obtain distillate containing the reaction product, namely a purified product of the reaction product. For further purification, this distillate is again distilled under reduced pressure at a temperature higher than that at which this distillate can be isolated from by-products, for example, at 120 to 130° C., to obtain a purified product containing the reaction product at a high concentration. The purity of the purified product thus obtained is generally more than 90% according to the analysis by gas chromatography. Further the yield to alkylcyclopentadiene is generally more than 40%.

According to the present invention, in this way, alkyl-substituted alkoxycarbonyltetracyclododecenes obtained by the Diels-Alder reaction of alkylcyclopentadienes and norbornenecarboxylic acid esters are a mixture of isomers having the abovementioned alkyl groups substituted at different positions. Further, such isomers include the abovementioned substitution position isomers as well as stereoisomers of each substitution position isomer, which makes a mixture of multi-component isomers. For example, the alkyl-8-alkoxycarbonyltetracyclo[4.4.0.1$^{2,5}$.1$^{7,10}$]dodeca-3-ene according to the present invention is a mixture of substitution position isomers comprising (Ia) position-3 alkyl substitution product

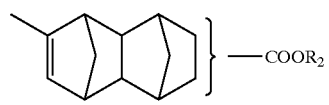

(Ib) position-2 alkyl substitution product, and

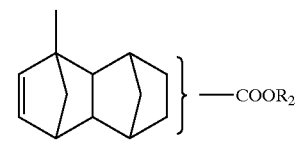

(Ic) position-11 alkyl substitution product.

In the formulae (Ia), (Ib) and (Ic) above, each parenthesis shows that the alkoxycarbonyl group substitution is at position 8 or position 9.

A (meth)acrylic acid addition product of alkyl-substituted tetracyclododecenecarboxylic acid ester represented by the abovementioned general formula (II) according to the present invention can be obtained by reacting an alkyl-substituted tetracyclododecenecarboxylic acid ester represented by the abovementioned general formula (I) and (meth)acrylic acid in the presence of an acid catalyst to carry out the addition reaction to the unsaturated bond (double bond) at position 3 of the alkyl-substituted 8-alkoxycarbonyltetracyclo[4.4.0.1$^{2,5}$.1$^{7,10}$]dodeca-3-ene, according to the present invention.

In this addition reaction, (meth)acrylic acid is generally used in the range of 0.05 to 1.0 molar part, preferably 0.1 to 0.3 molar part, per one molar part of the alkyl-substituted tetracyclododecenecarboxylic acid ester.

As for the abovementioned acid catalyst, a conventionally known catalyst, such as concentrated sulfuric acid, Nafion (perfluorosulfonic acid polymer, registered trade mark, Dupont), trifluoracetic acid, and trifluoromethanesulfonic acid can be used. In particular, concentrated sulfuric acid and Nafion (registered trade mark, Dupont) are preferably used. Such acid catalysts are generally used in the range of 0.05 to 0.4 part by weight, preferably 0.1 to 0.3 part by weight, per one part by weight of the alkyl-substituted tetracyclododecenecarboxylic acid ester.

The temperature for the abovementioned addition reaction is generally in the range of 10 to 80° C., preferably 20 to 40° C. The reaction can be carried out either under normal pressure or under pressure. Under these reaction conditions, the reaction is generally completed in 1 to 12 hours.

In the abovementioned addition reaction, no reaction solvent is generally needed. However, for example, aromatic hydrocarbons may be appropriately used as a reaction solvent. Further, in the reaction, a thermal-polymerization preventing agent, such as hydroquinone and 4-methoxyphenol, can be added to the reaction system.

The abovementioned addition reaction can also be carried out by either a batch system or a continuous system. In a batch system, for example, specified amounts of alkyl-substituted 8-alkoxycarbonyltetracyclododecenecarboxylic acid ester, (meth)acrylic acid and acid catalyst are placed together in a reaction container and reacted by heating.

The reaction product obtained by the addition reaction of the alkyl-substituted tetracyclododecenecarboxylic acid ester and (meth)acrylic acid is also purified, if necessary. For example, after the reaction is completed, cold water and an organic solvent such as toluene are added to the resulting reaction mixture and the reaction product is extracted into the oil layer and isolated from the reaction mixture, after which the oil layer containing the reaction product is washed, isolated and concentrated under reduced pressure to obtain a purified product of the reaction product. Further, if necessary, the resulting purified product is subjected to column isolation purification to obtain a further purified product.

The purified product of the (meth)acryl acid addition product of the alkyl-substituted tetracyclododecenecarboxylic acid ester thus obtained generally has a purity of more than 90% according to the analysis by gas chromatography. Further the yield to the alkyl-substituted tetracyclododecenecarboxylic acid ester is generally more than 30%.

The (meth)acrylic acid addition product of the alkyl-substituted tetracyclododecenecarboxylic acid ester thus obtained is also a mixture of isomers which have alkyl groups substituted at different positions and (meth)acryloyl groups substituted at position 3 or position 4. Further, such isomers include the abovementioned substitution position isomers as well as stereoisomers of each substitution position isomer, which makes a mixture of multi-component isomers. For example, according to the present invention, an (meth)alkyl acid addition product of the alkyltetracyclo[4.4.0.1$^{2,5}$.1$^{7,10}$]dodeca-3-ene represented by the abovementioned general formula (II), namely alkyl-8-alkoxycarbonyltetracyclo[4.4.0.1$^{2,5}$.1$^{7,10}$]dod (meth)acrylate is a mixture of substitution position isomers comprising (IIa) 3-alkyl-4-(meth)acryloyl substitution product

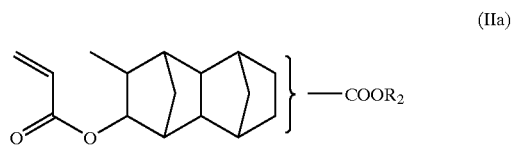

(IIb) 4-alkyl-4-(meth)acryloyl substitution product

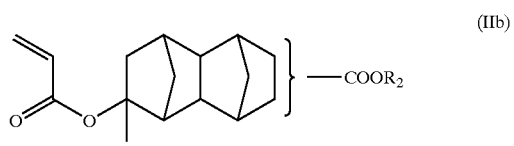

(IIc) 2-alkyl-4-(meth)acryloyl substitution product

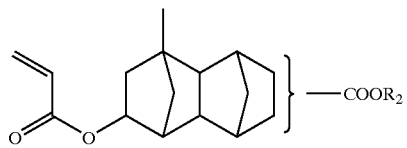
(IIc)

(IId) 5-alkyl-4-(meth)acryloyl substitution product, and

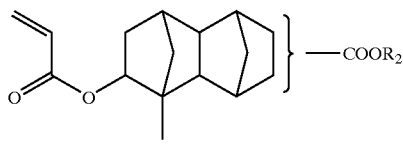
(IId)

(IIe) 11-alkyl-4-(meth)acryloyl substitution product

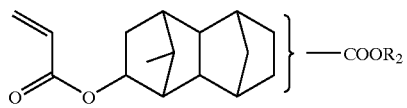
(IIe)

In the abovementioned formulae (IIa) through (IIe), each parenthesis shows that the alkoxycarbonyl group substitution is at position 8 or position 9.

Since tetracyclododecenecarboxylic acid esters and acryl acid addition products of these tetracyclododecenecarboxylic acid esters according to the present invention have an alkyl group as well as a carboxylic acid ester group or (meta)acryloyl group on a bulky bridged cyclic hydrocarbon skeleton, they are useful, for example, as a photosensitive resist material for semiconductor fine processing or the like and a material for optical material resins.

EXAMPLES

The present invention is further illustrated by the following examples that are not intended as a limitation of the invention.

Example 1
(Production of methyl-8-methoxycarbonyltetracyclo[4.4.0.1$^{2,5}$.1$^{7,10}$]dodeca-3-ene (1))

42.2 g of methylcyclopentadiene dimer (reagent grade) and 40.1 g of 5-methoxycarbonylbicyclo[2.2.1]hept-2-ene (97.1% pure according to gas chromatography analysis, a mixture of endo-type and exo-type) were placed in a 200-ml pressure-resistant glass container and reacted at 190° C. for 3 hours.

After the reaction was completed, the resulting reaction mixture was distilled at about 60° C. under reduced pressure, i.e., 130 to 260 Pa, and unreacted methylcyclopentadiene dimer and 5-methoxycarbonylbicyclo[2.2.1]hept-2-ene were distilled out. The resulting residue was again distilled at about 120° C. under reduced pressure of 130 to 260 Pa to obtain the main distillate containing the target product. This major distillate was further distilled at about 130° C. under the reduced pressure of 270 to 670 Pa to obtain 27.4 g of distillate.

This distillate was the targeted methyl-8-methoxycarbonyltetracyclo[4.4.0.1$^{2,5}$.1$^{7,10}$]dodeca-3-ene. The product was 94% pure and the yield to methylcyclopentadiene was 45%.

Molecular weight: 232 (according to mass spectrometry)
$^1$H-NMR spectrum (400 MHz; solvent: CDCl$_3$, δ (ppm)): shown in FIG. 1.

Example 2
(Production of methyl-8-methoxycarbonyltetracyclo(4.4.0.1$^{2,5}$.1$^{7,10}$)dodecanyl acrylate (11))

10 g of methyl-8-methoxycarbonyltetracyclo[4.4.0.1$^{2,5}$.1$^{7,10}$]dodeca-3-ene obtained in Example 1, 14.8 ml of acrylic acid and 0.46 ml of concentrated sulfuric acid were placed in a 200-ml glass container and reacted at 30° C. for 6 hours.

After the reaction was completed, ice water and toluene were added to the resulting reaction mixture, the admixture was stirred, and the oil layer containing the reaction product was isolated from the water layer. This oil layer was washed with an aqueous saturated sodium hydrogenbicarbonate solution and then an aqueous saturated sodium chloride solution, after which the layers were separated and the resulting oil layer was dried on magnesium sulfate. Next, the abovementioned oil layer was distilled under reduced pressure to distilled out toluene and thus an oily crude product containing the target product was obtained.

This crude product was subjected to column chromatography using ethyl acetate and hexane to obtain 2.6 g of an oily purified product containing the target product. This oily purified product was the targeted methyl-8-methoxycarbonyltetracyclo[4.4.0.1$^{2,5}$.1$^{7,10}$]-dodecanyl acrylate and had a purity of 95% according to gas chromatography analysis and the yield to methyl-8-methoxycarbonyltetracyclo[4.4.0.1$^{2,5}$.1$^{7,10}$]dodeca-3-ene was 20%.

Figure 2:
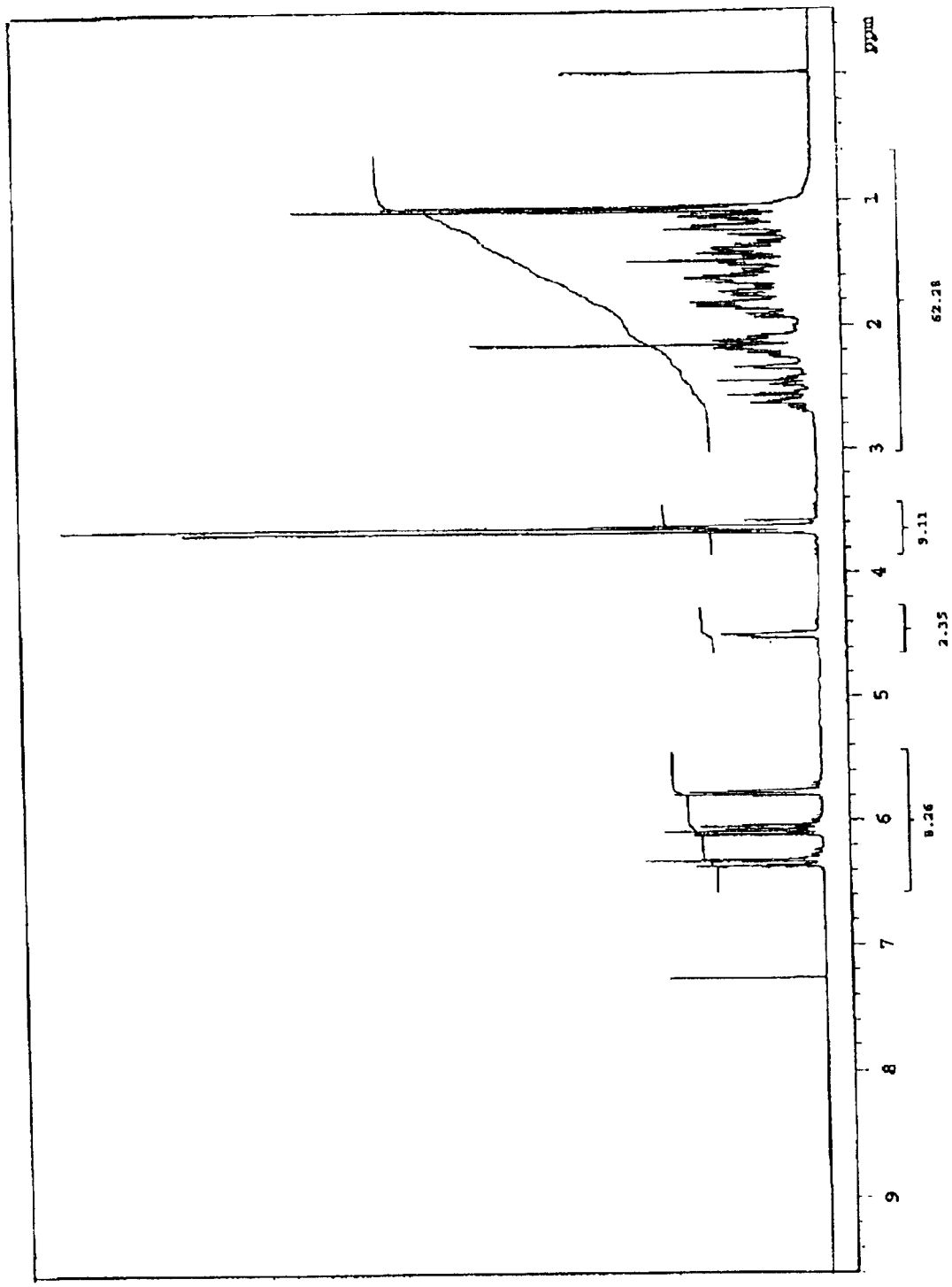
FIG. 2 shows the $^1$H-NMR spectrum of methyl-8-methoxycarbonyltetracyclo[4.4.0.1$^{2,5}$.1$^{7,10}$]dodecanyl acrylate.

Molecular weight: 304 (according to mass spectrometry)
$^1$H-NMR spectrum (400 MHz; solvent: CDCl$_3$, δ (ppm)): shown in FIG. 2.

What is claimed is:
1. A (meth)acrylic acid addition product of an alkyl-substituted tetracyclododecenecarboxylic acid ester represented by the general formula (II):

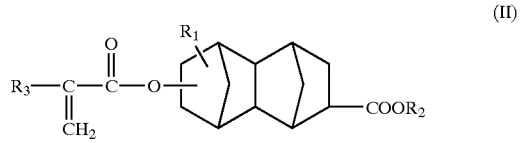
(II)

wherein $R_1$ is an alkyl group having 1 to 4 carbon atoms and $R_1$ is at position 2, 3, 4, 5 or 11 of the tetracyclododecenecarboxylic acid ester, $R_2$ is a hydrocarbon group having 1 to 12 carbon atoms, and $R_3$ is a hydrogen atom or a methyl group.

2. A method of producing a (meth)acrylic acid addition product of an alkyl-substituted tetracyclododecenecarboxylic acid ester represented by the general formula (II):

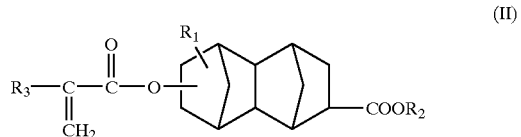
(II)

wherein $R_1$ is an alkyl group having 1 to 4 carbon atoms, $R_2$ is a hydrocarbon group having 1 to 12 carbon atoms, and $R_3$ is a hydrogen atom or a methyl group, comprising reacting an alkyl-substituted tetracyclododecenecarboxylic acid ester represented by the general formula (I) and (meth)acrylic acid in the presence of an acid catalyst:

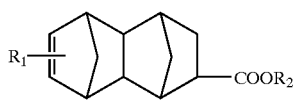
(I)

wherein $R_1$ is an alkyl group having 1 to 4 carbon atoms and $R_2$ is a hydrocarbon group having 1 to 12 carbon atoms.

3. An alkyl-substituted tetracyclododecenecarboxylic acid ester represented by the general formula (I):

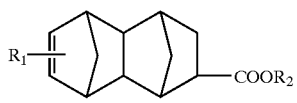
(I)

wherein $R_1$ is an alkyl group having 1 to 4 carbon atoms and $R_2$ is a hydrocarbon group having 1 to 12 carbon atoms.

4. A method of producing an alkyl-substituted tetracyclododecenecarboxylic acid ester according to claim 3, comprising subjecting to the Diels-Alder reaction an alkylcyclopentadiene represented by the general formula (III):

(III)

wherein $R_1$ is an alkyl group having 1 to 4 carbon atoms, and a norbornenecarboxylic acid ester represented by the general formula (IV):

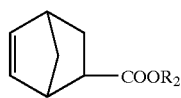
(IV)

wherein $R_2$ is a hydrocarbon group having 1 to 12 carbon atoms.

5. An acrylic acid addition product of a methyl-substituted tetracyclododecenecarboxylic acid ester represented by one selected from the group consisting of the following general formulae (IIa) to (IIe):

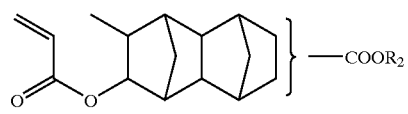
(IIa)

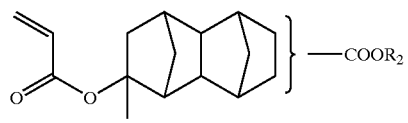
(IIb)

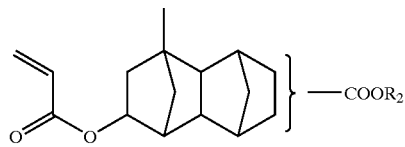
(IIc)

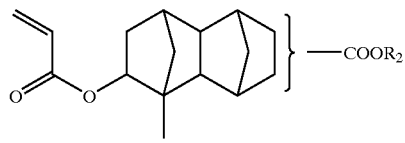
(IId)

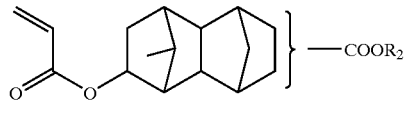
(IIe)

wherein $R_2$ is a hydrocarbon group having 1 to 12 carbon atoms, each parenthesis indicates that—$COOR_2$ is at position 8 or position 9.

6. An acrylic acid addition product of a methyl-substituted tetracyclododecenecarboxylic acid ester represented by the general formulae (IIb):

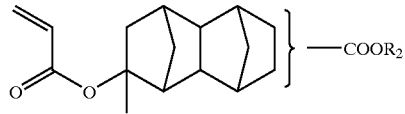
(IIb)

wherein $R_2$ is a hydrocarbon group having 1 to 12 carbon atoms, a parenthesis indicates that—$COOR_2$ is at position 8 or position 9.

7. A methyl-substituted tetracyclododecenecarboxylic acid ester represented by one selected from the group consisting of the following general formulae (Ia to Ic):

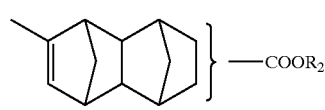
(Ia)

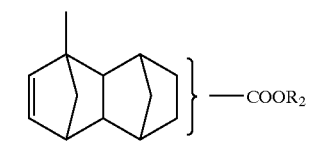
(Ib)

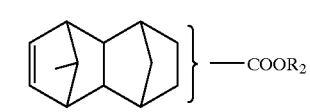
(Ic)

wherein $R_2$ is a hydrocarbon group having 1 to 12 carbon atoms, each parenthesis indicates that—$COOR_2$ is at position 8 or position 9.

* * * * *

UNITED STATES PATENT AND TRADEMARK OFFICE
CERTIFICATE OF CORRECTION

PATENT NO.        : 6,825,374 B2
APPLICATION NO. : 10/251725
DATED             : November 30, 2004
INVENTOR(S)       : Taiichi Shiomi and Takafumi Tsujigami It is certified that error appears in the above-identified patent and that said Letters Patent is hereby corrected as shown below:

At Column 2 in the Title page (Abstract) (57), line 7, please delete "represent" and insert -- present --, therefor.

At Column 14, line 39, In Claim 7, please delete "(Ia" and insert -- (Ia) --, therefor.

Signed and Sealed this

Sixth Day of March, 2007

JON W. DUDAS
*Director of the United States Patent and Trademark Office*